United States Patent [19]

Clayton et al.

[11] 3,941,774

[45] Mar. 2, 1976

[54] AMINOALKYL ESTERS OF PENICILLINS

[75] Inventors: John Peter Clayton; Kenneth David Hardy; Angela Wendy Capel Guest, all of Horsham, England

[73] Assignee: Beecham Group Limited, Great Britain

[22] Filed: May 21, 1973

[21] Appl. No.: 362,550

[30] Foreign Application Priority Data
May 25, 1972 United Kingdom............. 24668/72
Dec. 5, 1972 United Kingdom............. 56003/72

[52] U.S. Cl........... 260/239.1; 424/271; 260/243 C; 424/246

[51] Int. Cl.$^2$.............. C07D 499/44; C07D 501/20
[58] Field of Search................................ 260/239.1

[56] References Cited
UNITED STATES PATENTS
3,697,507   10/1972   Frederiksen et al............ 260/239.1

Primary Examiner—Nicholas S. Rizzo

[57] ABSTRACT

Novel substituted amino methyl esters of penicillins and cephalosporins for oral administration which are much better absorbed than the parent compounds.

8 Claims, No Drawings

AMINOALKYL ESTERS OF PENICILLINS

This invention relates to aminoalkyl esters of penicillins and cephalosporins and, when the compound contains a basic group to acid — addition salts thereof.

Penicillins and cephalosporins are widely used antibacterial agents and they are frequently administered orally if the absorption into the blood stream is sufficiently good. We have now found a group of aminoalkyl esters of penicillins and cephalosporins many of which are much better absorbed than the parent compound Accordingly the present invention provides a compound of formula (I):

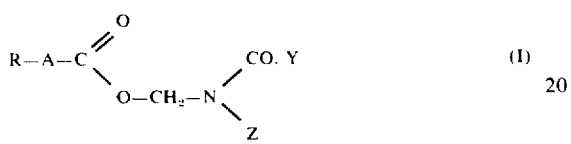

and acid addition salts thereof when a basic group is present wherein Y represents an alkyl, aryl, aralkyl, alkoxy, aralkoxy group; Z represents hydrogen or an alkyl cycloalkyl aryl, or aralkyl group- or Y + Z together with the —N—CO— group to which they are attached, is a heterocyclic ring; and A represents a group of formula (II) or (III):

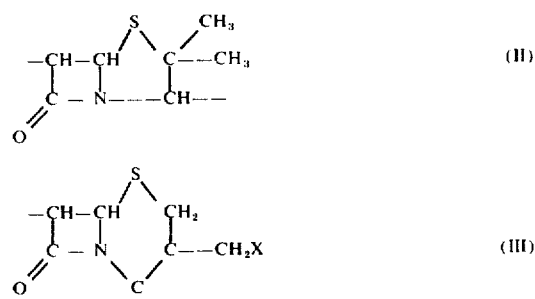

wherein

X represents hydrogen or an acetoxy or heterocyclicthio group;

and R is an organic acylamino group;

except that:

a. when Y + Z together with the —N—CO— group to which they are attached is a heterocyclic ring, then the group within the group Z which is joined to the N atom is not a carbonyl group; and b. when Z is hydrogen, Y is an alkoxy group and A is a group of formula (II), then R is not a group of formula (IV)

in which $R_1$ is $C_{2-7}$ alkyl, phenyl, substituted phenyl, thienyl or furyl.

By way of example, the group Y in formula (I) above may be lower alkyl, e.g. methyl, ethyl, n- and i-propyl, n-, sec-, iso- and t-butyl; aryl e.g. phenyl; aralkyl, e.g. benzyl, lower alkoxy, e.g. methoxy, ethoxy, n-and i-propoxy, n-, sec-, iso- and t-butoxy; aralkoxy, e.g. benzyloxy. The group Y is preferably an alkoxy or aralkoxy group.

Also by way of example, the group Z in formula (I) may be a lower alkyl, e.g. those groups exemplified for group Y above; cycloalkyl, e.g. cyclopentyl, cyclohexyl; aryl, e.g. phenyl.

The groups Y + Z in formula (I) together with the —N—CO— group to which they are attached may also form a heterocyclic ring. A preferred example of such a ring is the 3- benzoxazolidinone ring of formula (V):

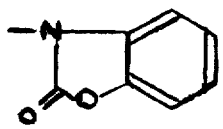

The radical R-A- in formula (I) is a 6-substituted penam-3 or 7-substituted cepham-4 radical. For the organic acylamino group, any of the acylamino side chains found in known antibacterially active penicillins and cephalosporins are suitable. For example, R in formula (I) may be phenyl-acetamido; 2- or 3-thienylacetamido; phenoxyacetamido, α-aminophenylacetamido; α-amino-2(or 3-) thienylacetamido, α-carboxyphenylacetamido; α-sulphophenyl- acetamido; α-azidophenylacetamido, α-guanidinophenylacetamido, or N-tetrazolylacetamido.

It will be clear that when the acylamino group R contains an asymmetric carbon atom, the compounds of this invention can exist in two optically active forms. This invention includes the pure epimers as well as mixtures of epimers.

The esters of this invention may be prepared by esterification of the carboxyl group of the corresponding penicillanic or cephalosporanic acid.

Thus, the invention also provides a process for the preparation of compounds (I) which process comprises reacting a compound of formula (VI):

or a reactive esterifying derivative thereof, in which formula R and A are as defined with respect to formula (I) above, with a compound of formula (VII):

or a reactive esterifying derivative thereof, in which formula Y and Z are as defined with respect to formula (I) above.

By the term "reactive esterifying derivative" in relation to compounds (VI) and (VII) above, we mean derivatives of (VI) and (VII) which when reacted together take part in a condensation reaction with the consequent formation of an ester linkage of formula (I).

Examples of reactive esterifying derivatives of compound (VI) includes salts, in particular the sodium, potassium and triethylammonium salts; acid halides, in particular the acid chloride; acid anhydride or mixed anhydrides, for example with a lower alkyl ester of carbonic acid; or the reactive intermediate formed with a carbodiimide or carbonyldiimidazole Examples of reactive esterifying derivatives of compound (VII) include alkylsulphonyl or arylsulphonyl esters; and halides of formula (VII A):

(VII A)

wherein W is a halogen atom and Y and Z are as defined with respect to formula (I). Preferred halides are the bromide, chloride and iodide. Usually it will be found satisfactory to react the sodium potassium or triethylammonium salt of a compound of formula (VI) with a halide of formula (VII A) in a solvent such as dimethyl formamide or acetone.

When the free acid of formula (VI) or a salt thereof is reacted with the hydroxyl compound (VII), the reaction is generally slow and inconvenient. Preferably, in such cases the hydroxy group is best converted to an alkylsulphonyl or arylsulphonyl ester. In this case the presence of a base is usually necessary to achieve high yields.

Another reactive esterifying derivative of compound (VI) is the acid halide particularly the acid chloride. This compound may be reacted with the hydroxy compound (VII) in the presence of an acid binding agent to prepare the desired ester of this invention.

When the group R in compound (VI) or its reactive esterifying derivative contains a free amino group this group should be protected before the esterification reaction.

Examples of protected amino groups include the protonated amino group ($NH_3^+$) which after the esterification reaction can be converted to a free amino group by simple neutralisation; the benzyloxycarbonylamino group or substituted benzyloxycarbonylamino groups which are subsequently converted to $NH_2$ by catalytic hydrogenation; and various groups which after the esterification reaction regenerate the amino group on mild acid hydrolysis (Alkaline hydrolysis is not generally useful since hydrolysis of the ester group takes place under alkaline conditions).

Examples of the group which may subsequently be converted to $NH_2$ by mild acid hydrolysis include enamine groups of general formula (VIII) or tautomeric modifications thereof, and α-hydroxyarylidene groups of general formula (IX) or tautomeric modifications thereof:

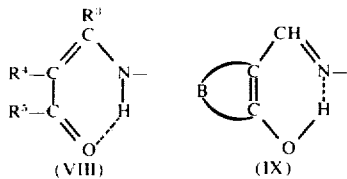

In structures (VIII) and (IX) the dotted lines represent hydrogen bonds. In structure (VIII) $R^3$ is a lower alkyl group, $R^4$ is either a hydrogen atom or together with $R^3$ completes a carbocyclic ring, and $R^5$ is a lower alkyl, aryl, or lower alkoxy group. In structure (IX) B represents the residue of a substituted or unsubstituted benzene or naphthalene ring.

An example of a protected amino which can be converted to $NH_2$ after the esterification reaction is the azido group. In this case the final conversion into $NH_2$ may be brought about by either catalytic hydrogenation or electrolytic reduction.

An alternative method of making compounds of this invention of formula (I) is by N-acylation of the corresponding esters of 6-aminopenicillanic acid or 7-aminocephalosporanic acid.

Thus, in another of its embodiments, this invention provides a method for the preparation of compounds of formula (I) which method comprises reacting a compound of formula (X) or a silyl derivative thereof:

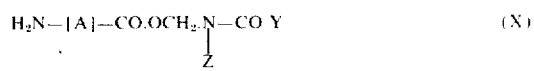
(X)

wherein A, Y and Z are as defined with respect to formula (I) above with a reactive N-acylating derivative of a compound of formula (XI):

$R_2 OH$ (XI)

wherein $R_2$ is an organic acyl group which may carry a protected amino group, removing the silyl group, if present, by hydrolysis or alcoholysis, and, if a protected amino group is present, optionally converting it to a free amino group under acid or neutral conditions.

By the term "silyl derivative" of the compound (X) we mean the product of the reaction betwen compound (X) and a silylating agent such as a halotrialkylsilane, a dihalodialkylsilane a halotrialkoxysilane, a dihalodialkoxysilane or a corresponding aryl or aralkyl silane and compounds such as hexamethyldisilazine. In general halotrialkylsilanes are preferred, especially trimethylchlorosilane. The silylated derivatives of the ester (X) are extremely sensitive to moisture and hydroxylic compounds, and after reaction with the reactive derivative of compound (XI) the silyl group of the intermediate acylated compound can be removed by hydrolysis or alcoholysis.

A reactive N-acylating derivative of the acid (XI) is employed in the above process. The choice of reactive derivative will of course be influenced by the chemical nature of the acyl group $R_2$.

Thus, when $R_2$ is acid stable or carries an acid group, such as the protonated amino group $NH_3^+$ or the azido group, it is often convenient to convert the acid (XI) into an acid halide for example by treating it with thionyl chloride or phosphorus pentachloride to give the acid chloride.

Such reagents would however be avoided when $R_2$ is an acid labile group or carries an acid labile group, e.g. of type (VIII) or (IX). In such cases it is often convenient to make use of a mixed anhydride. For this purpose particularly convenient mixed anhydrides are the alkoxyformic anhydrides, which are conveniently prepared by treating an alkali metal or tertiary amine salt of the acid (XI) with the appropriate alkyl chloroformate in an anhydrous medium at or below room temperature.

Other reactive N-acylating derivatives of the acid (XI) include the reactive intermediate formed on reaction in situ with a carbodiimide or carbonyldiimidazole.

The esters (X) used in the above process are also new compounds and also form part of this invention. They may be prepared by the first process described herein where R in formula (I) represents an amino group.

In particular compounds of formula (X) may be prepared though in poor yield, by direct coupling of 6-amino-penicillanic acid or 7-amino cephalosporanic acid with a compound of formula (VII A) in the presence of a base. With this process some epimerisation at $C_6$ or $C_7$ occurs and the process is therefore entirely satisfactory. Much better yields of compounds (X) can be achieved by coupling an N-protected derivative of 6-aminopenicillanic acid or 7-amino cephalosporanic acid (e.g. the triphenylmethyl derivative) with a compound of formula (VII A) and thereafter removing the protecting group (e.g. by mild acid hydrolysis in the case of the triphenylmethyl derivative).

Alternative types of N-protected 6-amino penicillanic acid are the 6-acylaminopenicillanic acids. Techniques for the removal of the 6-acyl side chain from benzylpenicillin and phenoxymethyl penicillin, for example, are well documented (of British Pat. No. 1,189,022) and generally involve treating an ester of the 6-acylaminopenicillanic acid with $PCl_5$ to form an imino chloride bond on the 6-amidonitrogen atom then treating the imino chloride with an alcohol to form an imino ether and then hydrolysing the amino bond to form the 6-aminopenicillanic acid ester. In the present case, it is possible to start from an ester of penicillin G or penicillin V [prepared for example by reaction of the sodium or potassium salt of the penicillin with a compound of formula (VII A)] and cleave the acyl side chain to prepare the corresponding ester of 6-aminopenicillanic acid.

Similarly, alternative types of N-protected 7 - amino cephalosporanic acid are the 7-acylaminocephalosporanic acids. Techniques for the removal of the 7-acyl side chain from cephalosporins are well known, and in the present case, it is possible to start with the appropriate ester of a 7-acylamino cephem, e.g. Cephalosporin C and remove the acyl side chain to form the ester of 7-aminocephalosporanic acid.

The following Examples illustrate methods for the preparation of some of the compounds of this invention.

EXAMPLE 1

(N-Ethoxycarbonyl-N-methyl) amino-methyl ester of Penicillin G

Penicillin G potassium salt (3.72 g.0.01 mol.) suspended in dimethylformamide (50 ml.) was treated with N-chloromethyl-N-methyl urethane (1.52g. 0.01 mol.) and the mixture stirred at room temperature for 2 hours. The solution was poured onto ice water (150 ml.) to produce a thick oil from which the supernatant liquid was decanted. The residual oil was dissolved in ethyl acetate (100 ml.) and washed with an aqueous solution of N sodium bicarbonate (10 ml.) followed by water (20 ml.).

The organic layer was dried over anhydrous magnesium sulphate and evaporated under reduced temperature and pressure. The residual oil crystallized to give 1.46g. (32.4%) of product as a colourless crystalline solid m.p. 78°-82°.

Found: C, 55.95; H, 6.09; N, 9.18; S, 7.02. $C_{21}H_{27}N_3O_6S$. Requires: C, 56.10; H, 6.05; N, 9.34; S, 7.14. N.m.r. $(CD_3)_2$ SO δ = 1.19 (3 H t. C$\underline{H_3}$CH$_2$O—), 1.52 (6H.d. gemdimethyls), 2.96 (3H.s. CH$_3$—N=), 3.56(2H.s. Ph C$\underline{H_2}$ CO—), 4.10 (2H.q. C$\underline{H_3}$CH$_2$ O—), 4.37 (1 H.s. C$_3$ proton), 5.47 4 H.m. (β lactam protons + —O.C$\underline{H_2}$.N=), 7.29 (5H.s. aromatic),8.8 (1 H.m.—CON$\underline{H}$—) p.p.m.

EXAMPLE 2

(N-Ethoxycarbonyl-N-methyl)amino-methyl ester of Cephalothin

Cephalothin [Sodium 7-(thiophene-2-acetamido) cephalosporante] (8.36 g.O. 02. mol.) in dimethylformamide. (60 ml.) was treated with N-chloromethyl-N-methylurethane (3g.0.02 mol.) in dimethylformamide (10 ml.) and stirred for 1 hour at room temperature. The mixture was poured, with stirring, into ice water (300 ml.). The precipitated solid filtered, washed well with water and dissolved in ethyl acetate (60 ml.). The solution was washed with a solution of N sodium bicarbonate (20 ml.) followed by water (40 ml.) and dried over anhydrous magnesium sulphate. The dried solution was evaporated under reduced temperature and pressure and the oily residue dissolved in dry benzene (20 ml.). The solution was diluted with dry ether until hazy and allowed to crystallise. The solid product was filtered, washed with ether and dried in vacuo to give the required ester 3.73 g. (36.3%) as a colourless crystaline solid m.p. 110°-112°.

Found: C, 49.40; H, 5.06; N, 8.14; S, 12.62 $C_{21}H_{25}O_8N_3S_2$; requires: C 49.30; H 4.93; N, 8.21; S, 12.53. N.m.r. $(CD_3)_2$ SO δ = 1.18 (3H.t. C$\underline{H_3}$ - CH$_2$-), 2.03 (3H.s.C$\underline{H_3}$ CO-), 2.94(3H.s. C$\underline{H_3}$.N=), 3.59 (2H.s. C$_2$ protons), 3.78

(2H.s. thiophene-C$\underline{H_2}$), 4.09 (2H.q.—OC$\underline{H_2}$.CH$_3$), 4.65 and 4.98(2H.q.—C$\underline{H_2}$ OCOCH$_3$), 5.09 & 5.17 (1 H.d. C$_6$ proton), 5.51 (2$\overline{H}$.s. —OCH$_2$—N=), 5.73 (1H.m. C$_7$ proton), 6.92 (2H.d. thiophene protons), 7.33 (1H.m. thiophene proton), 9.05 (1 H.d. —CO N$\underline{H}$ —) p.p.m.

EXAMPLE 3

(N-Benzyloxycarbonyl-N-methyl)aminomethyl ester of Cephalothin.

Cephalothin (4.18 g 0.01 mol.) in dimethylformamide (25 ml) was treated with a solution of benzyl N-chloromethyl N-methyl carbamate (2.13 g 0.01 mol) in dimethylformamide and stirred for 1 hr at room temperature. The product was isolated as described in Example 1:

to give the ester 3.07 g (53.6%) as a colorless cyrstalline solid. Recrystallisation from ethyl acetate/ether gave material m.p. 122°–124°. Found:C 54.49; H, 4.77; N 7.22 S 11.14 $C_{26}H_{27}N_3O_8S_2$ requires: C, 54.45; H 4.74; N 7.32 S 11.18 N.m.r. $(CD_3)$ SO: δ = 2.0 (3Hs. C$\underline{H_3}$ CO—) 2.99 (3Hs. C$\underline{H_3}$ N=)3.60 (2Hs C$_2$ protons) 3.78

(2Hs thiophene-C$\underline{H_2}$-)

4.65 and 4.98 (2Hq —C$\underline{H_2}$OCOCH$_3$) 5.14 (3H.m. C$_6$ proton + PhCH$_2$—) 5.55 (2Hs COOCH$_2$N=) 5.72 (1Hm C$_7$ proton) 6.93 (2Hd. thiophene protons) 7.37 (6Hm aromatic protons + thiophene proton) 9.03

(1Hd—CONH-) ppm.

EXAMPLE 4

(N-Ethoxycarbonyl-N-ethyl)aminomethyl ester of Cephalothin

Cephalothin (8.36 g 0.02 mol.) in dimethylformamide (50 ml) was treated with a solution of N-chloromethyl-N-ethylurethane (3.3 g 0.02 mol.) in dimethylformamide (10 ml) and stirred 1 hr at room temperature. The product was isolated as described in Example 1 to give 3.47 g (33.1% of colourless crystalline solid m.p. 108°–110° Found: C, 50.08; H, 5.16 N 8.06 S 12.20 $C_{22}H_{27}N_3O_8S_2$ requires: C 50.25; H, 5.18; N, 8.00; S, 12.20 N.m.r. $(CD_3)_2$ SO: δ = 1.15 (6Hm. 2 × $\underline{CH_3}$ $CH_2$—) 2.04 (3Hs $\underline{CH_3}$ CO—) 3.26 and 3.50 (2Hq = $\underline{NCH_2}$ $CH_3$) 3.61 (2Hs $C_2$ protons) 3.80

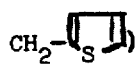

4.0 and 4.24 (2Hq —$\underline{OCH_2}$ $CH_3$) 4.68 and 5.0 (2Hq —$\underline{CH_2}$ $OCOCH_3$) 5.17 (1Hd. $C_6$proton) 5.54 (2$\underline{Hs}$.—$CH_2N=$) 5.57 (1Hm. $C_7$ proton) 6.95 (2Hd. thiophene protons) 7.37 (1Hm thiophene proton) 9.08 (1Hd.—CO$\underline{NH}$—) ppm.

EXAMPLE 5

(N-n-Butyl-N-ethoxycarbonyl)aminomethyl ester of Cephalothin

Cephalothin (4.18 g 0.01 mole) in dimethylformamide (15 ml) was treated with N-n-butyl-N-chlormethylurethane (1.9 g) and stirred for 1.5 hr at room temperature. The product was isolated as described in Example 1 and crystallised from other to give 1.97 g (35%) of the required material Found: C, 51.53; H, 5.63; N, 7.42; S, 11.36 $C_{24}H_{31}N_3O_8S_2$; requires: C, 52.05; H,5.64 N, 7.59; S, 11.58. N.m.r. $(CD_3)_2$ SO; δ = 0.8–1.5 (10H,m. ester $CH_3$, butyl $CH_3$ 2 × butyl $CH_2$) 2.03 (3H.s. COCH$_3$), 3.32 (2H t, N—CH$_2$), 3.79

3.60 (2H.s. S—CH$_2$), 4.11 (2H, q ester CH$_2$) 4.85 (2H. d, $\underline{CH_2}$ OCOCH$_3$) 5.16 (1H,d, $C_6$ proton) 5.53 (2H,s, O—$\underline{CH_2}$ —N), 5.8 (1H,m,$C_7$ proton) 6.96 (2H,d, thiophene protons) 7.37. (1H,q, thiophene protons) 9.04 (1H,d, CONH) ppm.

EXAMPLE 6

(N-Cyclohexyl-N-ethoxycarbonyl)aminomethyl ester of Cephalothin

Cephalothin (8.36 g 0.02 mole) in dimethylformamide (40 ml) was treated with N-chloromethyl N-cyclohexyl urethane (4.4 g 0.02 mole) and stirred at room temperature for 1.5 hr. The product was isolated by the procedure described in Example 1 and crystallised from ether to give 3.65 g (31%) of the required material. Found: C, 52.03; H, 5.74; N, 6.92; S, 10.39 $C_{23}H_{33}N_3O_8S_2$ requires C, 53.88; H, 5.74; N, 7.24; S, 11.06 N.m.r. $(CD_3)_2$ SO: δ = 1.19 (3H,m, ester CH$_3$) 1.0 to 2.0 (11H, broad multiplet, cyclohexyl protons), 2.03 (3H,s, —COCH$_3$) 3.59 (2H,s, —SCH$_2$) 3.81

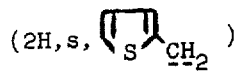

4.06 (2H,q, ester CH$_2$) 4.82 (2H,m, $\underline{CH_2}$ OCOCH$_3$) 5.18 (1H,m,$C_6$ proton)5.56 (2H,s, $\overline{OCH_2N}$<) 5.8 (1H,m, $C_7$ proton)6.96 (2H,d, thiophene protons) 7.4. (1H,t, thiophene proton) 9.04 (1H,d, CONH)ppm.

EXAMPLE 7

(N-Ethoxycarbonyl-N-phenyl)aminomethyl ester of Cephalothin

Cephalothin (4.16 g 0.01 mole) in dimethylformamide (10ml) was treated with N-chloromethyl-N-phenyl urethane (1.8 g 0.01 mole) and stirred for 1.5 hr at room temperature. The product was isolated as described in Example 1 and recrystallised from benzene and ether to give 2.91 g (51%) of material m.p. 140°–142°C. Found: C, 54.38; H, 4.80; N, 7.16; S, 11.11 $C_{26}H_{27}N_3O_8S_2$ requires: C, 54.44, H, 4.74; N, 7.32; S, 11.18. Nm.r. $(CD_3)_2$ SO: δ = 1.16 (3H t, $\underline{CH_3}$—), 2.0 (3H, d, OCOCH$_3$)3.62 (2H,s, S—CH$_2$), 3.80

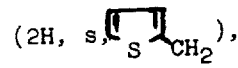

4. 16 (2H,q, —$\underline{OCH_2}$ CH$_3$) 4.63 (2H, s, $\underline{CH_2}$OCOCH$_3$), 5.13 (1H, s, $C_6$ proton) 5.72 (2H,s, -OCH$_2$N-), 5.80 (1H, s, $C_7$ proton), 6.96 (2H, d, thiophene protons), 7.35 (5H, s, phenyl), 7.42 (1H, s, thiophene proton) 9.2 (1H, d, CONH).

EXAMPLE 8

(N-Isobutyloxycarbonyl-N-methyl)aminomethyl ester of Cephalothin.

Cephalothin(4.18g.0.01 mole) in dimethylformamide (10 ml) was treated with isobutyl N-chloromethyl N-methyl carbamate (1.8 g 0.01 mole) and stirred for 1 hr at room temperature. The product was isolated as in Example 1 and crystallised from ether to give 2.01 g (37%) of the required material. Found: C, 50.69; H, 5.44; N, 7.61; S, 11.25. $C_{23}H_{29}N_3O_8S_2$ requires: C,51.21; H, 5.41; N, 7.78; S, 11.88. N.m.r. $CD_3)_2$ SO: δ = 0.88

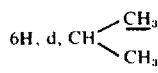

1.8 (1H,m. CH<) 2.01 (3H, s, CH$_3$CO), 2.96 (3H, s, N-CH$_3$), 3.60

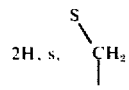

3.77 (2H, s,

3.89 (2H, s, $\underline{OCH_2}$CH<), 4.82 (2H, d, $\underline{CH_2}$O) 5.13 (1H, d, $C_6$ proton), b 5.53 (2H, s, OCH$_2$N), 5.77 (1H, m, $C_7$ proton) 6.94 (2H, d, thiophene protons), 7.39 (1H, t, thiophene proton) 9.09 (1H, d, CONH) ppm.

EXAMPLE 9

N-Benzoylaminomethyl ester of Cephalothin

Cephalothin (8.32 g. 0.02M) in anhydrous dimethylformamide (15 ml) was treated with N-chloromethylbenzamide (3.40 g 0.02M). The mixture was stirred at room temperature for two hours then poured onto ice and water (150 ml). The oily precipitate was dissolved in ethyl acetate (100 ml) and the aqueous solution was extracted with ethyl acetate (50 ml). The combined organic layers were washed with 0.5N sodium bicarbonate solution (40 ml). A white solid began to crystallise out; this was collected and dried in vacuo 3.2 g, m.p. 147°–148°. The ethyl acetate solution was separated from the bicarbonate solution, washed with saturated brine and dried over anhydrous magnesium sulphate. The drying agent was removed and the organic solution evaporated to dryness to give a white solid, 3.3 g, m.p. 148°–150°. The total yield, 6.5 g, was recrystallised from acetone and ether to give the ester, 3.20 g, 30%, m.p. 154°–156°. N.m.r. [$(CD_3)_2SO$], δ = 8.1–7.3 (5H, m, aromatic protons), 7.3–6.9 (3H, m, thiophene protons), 6.0–5.5 (3H, m, $C_7$ and ester methylene protons) 5.12 and 4.90 (2H, q,—$CH_2OCOCH_3$), 5.02 (1H, d, $C_6$ proton), 3.85

(2H, s, 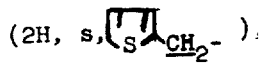 )

3.48(2H, m, $C_2$ methylene protons), 2.03 (3H, s, —$CH_2$ $OCOCH_3$).U.V. (95% EtOH)$\lambda_{max}$232 ($\epsilon$ = 20,544) and 264mm ($\epsilon$ = 8,166)

EXAMPLE 10

N-Benzoylaminomethyl ester of penicillin G

Potassium penicillin G (11.1 g, 0.03M) in anhydrous dimethylformamide (20 ml) was treated with N-chloromethyl-N-methylbenzamide (5.10 g, 0.03M). The mixture was stirred at room temperature for two hours then poured onto ice and water (250 ml) and extracted with ethyl acetate (3 × 100ml). The combined extracts were washed with 0.5N sodium bicarbonate solution (60 ml) and saturated brine (100 ml) and then dried over anhydrous magnesium sulphate. The filtered solution was concentrated to a small volume and the white crystalline solid collected, 10.00 g 71.4% m.p. 124°–127°. Recrystallised from ethyl acetate and ether, m.p. 128°–130°. N.M.R. ($CDCl_3$) δ = 8.2–7.2.— (10H, m, aromatic protons). 5.8–5.4. (4h, m, β-lactam and ester methylene protons), 4.36 (1H, s, $C_3$ proton), 3.59 (2H, s, Ph$CH_2$ CO—), 1.42 (6H, s, gemdimethyl protons)ppm. Found: C, 61.71; H, 5.59; N, 9.06; S, 6.90. $C_{24}H_{25}N_3O_5S$ requires: C, 61.65; H 5.39, N, 8.99; S, 6.86.

EXAMPLE 11

N-Benzoylaminomethyl ester of penicillin G

Penicillin G potassium salt (3.78 g, 0.01 mole) in dry acetone (30 ml) was cooled to −10° and treated with ethyl chloroformate (0.96 ml) and pyridine (1 drop). The mixture was stirred at −10° for 0.5 hr and treated with a solution of N-hydroxymethylbenzamide (1.51 g, 0.01 mole) in dry acetone (20 ml). The reaction was stirred at room temperature for 1 hr. The mixture was filtered and the clear filtrate evaporated. The residue was dissolved in ethyl acetate, washed with N sodium bicarbonate (10 ml) followed by water (2 × 10 ml), dried and evaporated. The residue was diluted with ethyl acetate (2 vols) followed by dry ether until the solution became hazy and allowed to crystallise. The product was obtained as a colorless crystalline solid 1.91 g (41.5%) m.p. 127°–128° (d) I.r. and n.m.r. were identical with the product obtained in Example 10.

EXAMPLE 12

3-Benzoxazolidinone methyl ester of penicillin G

Potassium penicillin G (3.73 g 0.01 mole) in dry acetone (30 ml), cooled to −10°, was treated with ethyl chloroformate (0.96 ml) and pyridine (2 drops) and stirred 0.5 hr at −10°. A solution of 3-hydroxymethylbenzoxazolidinone (1.65 g, 0.01 mole) in dry acetone (20 ml) was added and the mixture stirred at room temperature for 1.05 hours. The mixture was filtered through Celite and the filtrate evaporated. The residue was dissolved in ethyl acetate (50 ml) washed with N sodium bicarbonate (10 ml). followed by water (2 × 20 ml), dried over anhydrous magnesium sulphate and evaporated in vacuo. The oily residue was dissolved in benzene, diluted with dry ether and allowed to crystallise. The product 1.34 g (26.7%) was obtained as a colourless crystalline solid m.p. 157°–159°. N.m.r. ($CD_3$) SO: δ = 1.36 and 1.59 (6H,d, gemdimethyls), 3.58 (2H,s, Ph$CH_2$—) 4.48 (1H,s,$C_3$ proton) 5.54(2H,m. β-lactam protons) 6.02 (2H, s,O$CH_2$N) 7.28 (9H, m, aromatic protons)ppm. Found: C 60.22; H, 5.06; N, 8.72; S, 6.31. $C_{24}H_{23}O_6N_3S$ requires: C, 59.87; H, 4.81; N, 8.73; S, 6.65.

EXAMPLE 13

3-Benzoxazolidinonemethyl ester of penicilling G

Potassium penicillin G (1.86 g. 0.005 mol.) in dimethylformamide (10 ml.) cooled to 0° was treated with a solution 3-chloromethyl-benzoxazolidinone (0.91 g. 0.005 mol) in dimethylformamide and stirred at room temperature for 1 hr. The mixture was poured onto ice water (100 ml) and the precipitated solid filtered, washed with water and dried. The solid was recrystallised from benzene/ether to give the required ester 1.8 g. (74.9%) as a colourless crystalline solid mp. 166°–168°. This material was identical with that obtained in Example 12 as shown by n.m.r.

EXAMPLE 14

(N-Acetyl-N-methyl)aminomethyl ester of penicillin G

Penicillin G potassium salt (7.46 g 0.02 mol.) suspended in dimethylformamide (30 ml.) was cooled to 0° and treated with N-chloromethyl N-methylacetamide (2.64 g. 0.02 mol.) in dimethylformamide (10 ml.). The mixture was stirred at 0° for 1.05 hrs. and poured onto ice water (300 ml). The precipitated oil was dissolved in ethylacetate (100 ml.), washed with N-sodium bicarbonate solution (20 ml) followed by water (10 ml) dried over anhydrous magnesium sulphate and evaporated to small volume. The residue was diluted with dry ether and allowed to crystallise. The product was filtered, washed with dry ether and dried in vacuo to give the required ester 4.77 g. (56.9%) as a colourless crystalline solid mp. 92° (d). Found: C, 57.25 H, 5.96; N, 9.88; S, 7.66 $C_{20}H_{25}N_3O_5S$ requires:

C, 57.26; H, 6.01; N, 10.02; S, 7.64. N.m.r. (CDCl₃) δ =1.46 (6H s. gem dimethyls), 2.19 (3H.m.-COCH₃), 3.09 (3H.d. CH₃N=), 3.64 (2H.s. Ph. CH₂-), 4.40 (1H.s. C₃ proton), 5.55 (4 H.m. β-lactam protons +—O. CH₂ N=), 7.31 (5H s. aromatic protons).

EXAMPLE 15

N-Benzoyl-N-methylaminomethyl ester of cephalothin

Cephalothin sodium salt (6.35 g. 0.015 mol.) suspended in dimethylformamide (30 ml) was cooled to 0° and treated with N-chloromethyl-N-benzoylmethylamine (2.8 g 0.015 mol.) The mixture was stirred 1 hr. at 0° and poured onto ice water (200 ml.). The product was isolated as described in Example 2 to give the ester from benzene/ether 5.29 g. (65%) as a colorless crystalline solid mp. 138°–140°. Found: C, 54.70; H, 4.63; N 7.82; S, 11.65. C₂₅H₂₅N₃O₇S₂ requires C, 55.24; N, 4.63; N, 7.73; S, 1180. N.m.r. [(CD₃)₂SO] δ= 2.04 (3H.s. CH₃CO) 3.07 (3H.s. CH₃N=), 3.64 (2H s. C₂ Methylene), 3.81

(2H.s. 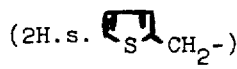 )

4.86. (2H.d. -CH₂ OCOCH₃), 5.20 ( 1H.d. C₆ proton), 5.56 (2H s —COOCH₂N=) 5.7 (1H m. C₇ proton) 6.96 (2H.d. thiophene protons) 7.34 (1H.m. thiophene proton), 7.49 (5H s aromatic protons), 9.12 (1H m. —CONH—).

EXAMPLE 16

N-Acetylaminomethyl ester of penicillin G

Potassium penicillin G (3.72 g 0.01 mol.) was stirred in anhydrous ethyl acetate (20 ml.) and cooled to −10°. N-Methyl morpholine (1 drop) was added followed by ethyl chloroformate (0.096 ml 0.01 mol.) and the mixture stirred −10° for 15 minutes. Hydroxymethyllactamide (0.89 g 0.01 mol) suspended in ethyl acetate (20 ml) was added all at once and the mixture stirred at room temperature for 2.05 hrs. The product was isolated as described in Example 11 to give 1.21 g (24%) of colorless crystalline solid mp 130°. N.m.r. [CDCl₃ + (CD₃)₂SO] δ = 1.47 and 1.57 (6H.d. gem dimethyls), 2.00 (3H s —COCH₃ ) 3.65 (2H s PhCH₂CO—), 4.37 (1H.s C₃ proton), 5.30 [2H d (J=7Hz )—COCH₂NH—], 5.4–5.8 (2H.m β-lactam protons) 7.32 (5H s aromatic protons)

EXAMPLE 17

N-Propionylaminomethyl ester of penicillin G

Potassium penicillin G (7.56 g 0.02 mol ) in ethyl acetate (40 ml ) was converted to the mixed anhydride and reacted with hydroxymethyl propionamide (2.06 g. 0.02 mol.) as described in Example 16 to give the required ester from ethyl acetate/ether 3.54 (47%) as a colourless crystalline solid mp 128° N.m r (CDCl₃) δ=1.0–1.25 3H t —COCH₂ CH₃ ), 1.45 (6H s gem dimethyls), 2.00–2.4 (2H.q —COCH₂—) 3.65 (2H s PhCH₂CO-) 4.38 (1H.s. C₃ proton) 5.3 (2H.d. —COOCH₂NH—) 5.4–5.8 (2H m β-lactam protons) 7.35 (5H s. aromatic protons).

EXAMPLE 18

Isobutyloxycarbonyl-N-methylaminomethyl 7-(2-thienyl) acetamido-3-(2,methyl-1,3,4-thiadiazol-5-ylthio)-methyl ceph-3-em-4 carboxylate Sodium 7-(2-thienyl)acetamido-3-(2-methyl-1,3,4-thiadiazol-5-ylthio) methyl ceph-3-em-4carboxylate (3.3 g. 0.0067 mol) suspended in dimethylformamide (15 ml) was cooled to 0° and treated with chloromethyl N-methyl isobutylcarbamate (1.5 g) and triethylamine was added to attaim pH 8. The mixture was stirred at R.T. for 1 hr. and poured onto ice water (200 ml). The product was isolated as described in Example 2 and crystallised from benzene/ether to give the required ester 1.3 g (37.8%) as a colorless crystalline solid mp 106°–108° U.V. (95% EtOH) λₘₐₓ238.7 (ε= 14,984) and 273.5 nm (pound = 14,284) N.m.r. [(CD₃)₂SO] δ = 0.85 and 0.95 [6H d —CH(CH₃)₂] 1.90 [1H. M. —CH₂CH (CH₃)₂], 2.70 (3H.s. thiadiazole-2methyl), 3 0 (3H.s. =N—CH₃), 3.33 (2H m. C₂ methylene), 3.87 (4H m —OCH₂CH= and

), 4.42 (2H.q. —CH₂S—) 5.18 (1H d C₆; proton), 5.58 (2H.s.-CCH₂N=), 5.75 (1H m. C₇ proton), 6.97 (2H.d. thiophene protons), 7.40 (1H m. thiophene proton) 9.11 (1H d. —CONH—).

EXAMPLE 19

N-Isobutyryl-N-methylaminomethyl ester of cephalothin

Cephalothin sodium salt (4.18 g. 0.01 mol.) suspended in dimethylformamide (7 ml) was cooled to 0° and treated with N-chloromethyl N-isobutyrylmethylamine (1.49 g. 0.01 mol). The mixture was stirred at room temperature for 2.5 hrs. and poured onto ice water (200 ml). The product was isolated as described in Example 2 to give the ester from ethylacetate/ether 1.25 g (24.6%) as a colorless crystalline solid mp. 98°–100°. N.m.r [(CD₃)₂SO] δ= 1.04 [6H.d. —COCH (CH₃)₂], 2.04 (3H s —COCH₃), 2.8–3.4 [4H.m. = NCOCH(CH₃)₂ and = NCH₃] 3.62 (2H m C₂ methylene), 3.79

), 4.72 –5.01 (2Hq —CH₂OCO—), 5.17 (1H.d C₆ proton), 5.5–6.0 (3H.m. C₇ proton and —OCH₂N=) 6.9–7.5 (3H m thiophene protons) U.V. (95% EtOH) λₘₐₓ 238(ε= 12,454) and 265 nm (ε= 7.287)

EXAMPLE 20

Benzoxazolidinone-3methyl ester of 6-aminopenicillanic acid p-toluenesulphonate

6-Aminopenicillanic acid (2.16 g. 0.01 mol.) suspended in dimethylformamide (10 ml) was treated with triethylamine (2ml) and stirred at room temperature for 0.5 hr. 3-Chloromethylbenzoxazolidinone (1.83 g. 0.01 mol.) dissolved in dimethylformamide (10 ml) was added at 0° and the mixture stirred for 3.15 hrs at room temperature. The mixture was diluted with ethyl acetate (30 ml.) and filtered. The clear filtrate was washed with water (4×15 ml) dried over anhydrous magnesium sulphate and treated with a solution of p-toluenesulphonic acid (1.7 g. 0.009 mol) in ethyl acetate (20 ml). The product was allowed to crystallise, filtered, washed with ethyl acetate and dried to give the ester salt 3.25 g (60.7%) as a colorless crystalline solid mp. 162° (d). Found C, 51.58; H, 4.90; N, 7.54; S, 11.59 $C_{23}H_{25}N_3O_8S_2$. requires C, 51.56; H, 4.71; N, 7.85; S, 11.97. Nm.r. [$(CD_3)_2SO$] δ= 1.38 and 1.60 (6H.d. gem dimethyls), 2.30 (3H.s. p-substituted -$CH_3$), 4.63 (1H.s. $C_3$proton), 5.16 (1H. d. $C_5$ proton) 5.56 (1H. d. $C_6$ proton), 6.04 (2H.s. —$CH_2N=$), 7.37 (8H m aromatic protons).

EXAMPLE 21

Benzoxazolidinone-3-methyl ester of ampicillin hydrochloride

Benzoxazolidinone-3-methyl ester of 6-aminopenicillanic acid p-toluene sulphonate (5.36 g. 0.01 mol.) was mixed with ethyl acetate (240 ml) and 2% sodium bicarbonate solution (160 ml) and well shaken. The aqueous layer was separated and the organic layer washed with water (110 ml) containing 2% sodium bicarbonate (6 ml). The organic layer was dried over anhydrous magnesium sulphate and evaporated. The residue, redissolved in ethyl acetate (60 ml.) was cooled to 0°. Sodium N-(1-methoxycarbonyl propen-2-yl) D-α-aminophenylacetate (5.4 g 0.02 mol) in ethyl acetate (80 ml) was cooled to −15° and treated with N-methylmorpholine (0.1. ml.) followed by ethyl chloroformate (1.92 ml 0.02. mol.) and stirred at −15° for 6 minutes. The ester base solution was added all at once and the mixture stirred for 10 minutes at −15° followed by 1 hr at room temperature. The reaction mixture was washed with 0.5N sodium bicarbonate (20 ml) followed by water (2×10 ml) dried over anhydrous magnesium sulphate and evaporated. The residue was dissolved in acetone (40 ml.) and water (36 ml.). The solution was stirred and adjusted to pH 2.5 with 5N HCl until constant (ca 0.5 hr.). The solution was evaporated to half volume to remove acetone and extracted with ethyl acetate (40 ml). This extract was diluted with petroleum/ether 40°–60° (32 ml) and extracted with water at pH 3.0 (10 ml). The combined aqueous layers were mixed with sodium chloride (10 g.) and the oily upper layer separated. The aqueous layer was extracted with ethyl acetate (20 ml) which was combined with the oil. This organic solution was dried over anhydrous magnesium sulphate and evaporated to half volume. Isopropanol, (40 ml) was added and evaporated to half volume. The residue was diluted with excess dry ether and the separated solid filtered, washed with ether and dried to give the product 2 g. (18.8%) as a colorless solid N m.r [$(CD_3)_2SO$] δ=1.25 and 1.43 (6H d. gem dimethyls) 4.45 (1H.s. $C_3$ protone) 5.21 (1H.s. α - proton) 5.50 (2H m β-lactam), 6.01 (2H.s. O$CH_2$N=), 7.40 (9H m aromatic protons), 9.09 (4H m. —NH protons)

EXAMPLE 22

Benzoxazolidinone-3-methyl ester of cephalothin

Cephalothin sodium salt (4.18 g. 0.01 mol.) suspended in dimethylformamide (15 ml.) was cooled to 0° and treated with a solution of N-chloromethyl benzoxazolidinone (1.65 g.) in dimethylformamide (15 ml). The mixture was stirred at room temperature for 1.5 hr. and poured onto ice water (200 ml). The product was isolated as described in Example 2 and crystallised from benzene/ether to give 1.23 g. (22.7%) as a colorless crystalline solid.

EXAMPLE 23

N-Ethoxycarbonyl-N-methylaminomethyl 7-[1-(1H)-tetrazolylacetamido]-3-[2'-(5'-methyl-1',-3',4'-thiadiazolyl)-thiomethyl]-ceph-3-em-4-carboxylate Cefazolin sodium salt (2.38 g. 0.005 mol.) suspended in dimethylformamide (10 ml) and cooled to 0° was treated with a solution of N-chloromethyl-N-methylurethane (0.76 g. 0.005 mol) in dimethylformamide. The mixture was stirred for 1 hr at room temperature and poured onto ice water (150 ml.). The product was isolated as described in Example 2 and crystallised from ethylacetate/petroleum ether 60°–80° to give the required ester 1.35 g (47.4%) as a colorless crystalline solid mp 114° (d) U.V. (95% EtOH) λ$_{max}$272 nm. (∈= 13,256). N.m.r. [$(CD_3)_2SO$] δ= 1.20 (3H. t. —O$CH_2CH_3$), 2.71 (3H.s. thiadiazole-5-methyl), 3.0 (3H s. = N$CH_3$), 3.78. (2H.m. $C_2$ methylene), 4.10 (2H.q. —O$CH_2CH_3$), 4.50 (2H m. —$CH_2S$—) 5.21 (1H.m. $C_6$ proton), 5.42 (2H s. =N$CH_2CO$—) 5.52 (2H s - O$CH_2N=$) 5.80(1H.m $C_7$ proton) 9.38 (1H.s. tetrazole methine) 9.50 (1H.d —CO$NH$—)

BIOOGICAL DATA

EXAMPLE 24

Blood Levels in Squirrel Monkeys

Squirrel Monkeys were dosed by the oral route at a dose equivalent to 100mg/kg of the parent antibiotic free acid and assayed against *Sarcina Lutea* in terms of parent antibiotic. Table I shows the concentrations of antibiotic in the blood at 0.25 1.0 2.0 4.0 and 6.0 hours after dosing for several compounds of the invention

TABLE I

| Compound of Example No | Concentratin μg/ml at hours after dosing | | | | | |
|---|---|---|---|---|---|---|
| | 0.25 | 0.5 | 1.0 | 2.0 | 4.0 | 6.0 |
| 1 | 17.2 | 17.2 | 12.1 | 5.3 | 0.54 | 0.08 |
| 4 | 0.49 | 1.38 | 1.98 | 1.65 | 1.17 | 0.17 |
| 5 | 0.31 | 1.96 | 2.0 | 1.23 | 0.12 | 0.1 |
| 6 | 4.7 | 6.2 | 3.8 | 1.5 | 0.18 | 0.1 |
| 8 | 2.2 | 7.2 | 4.99 | 2.1 | 0.97 | 0.5 |
| 14 | 3.7 | 5.06 | 2.4 | 0.7 | 0.15 | 0.07 |
| 16 | 1.57 | 1.54 | 1.01 | 0.83 | 0.36 | 0.19 |
| 17 | 1.51 | 1.43 | 1.31 | 0.89 | 0.34 | 0.11 |
| 19 | 1.4 | 1.8 | 2.1 | 1.5 | 0.33 | 0.2 |

EXAMPLE 25

Hydrolysis of Esters

The esters were incubated at the equivalent concentration (μg /ml) of The parent antibiotic at 37° in pH2 HCl solution or pH 7.0 phosphate buffer or human blood, then separated and assayed by bio-electrophoresis. (The hydrolysis rates at pH 2.0 could not be measured for Pen G esters owing to rapid degradation of the Pen G formed The results for several compounds of the invention are shown in table II

TABLE II

| Compound of Example No | Concentration | Hydrolysing system | μg/ml parent antibiotic after: | | | |
|---|---|---|---|---|---|---|
| | | | 3 min | 8 min | 15 min | 25 min |
| 1 | 5μg/ml. | Phosphate buffer pH 7 | 3.5 | — | 3.6 | 3.4 |
| | | Human Blood | 2.3 | 2.9 | 3.7 | 3.7 |
| 2 | 80μg/ml. | HCl at pH 2 | 18.0 | 19.7 | 21.0 | 31.8 |
| | | Phosphate buffer pH 7 | 43 | 42 | 46 | 52 |
| 6 | 100μg/ml. | Phosphate pH 7 | 93 | 97 | 97 | 100 |
| | | HCl pH 2 | 66 | 67 | 67 | 72 |
| 8 | 100μg/ml. | Phosphate pH 7 | 148 | 148 | 148 | 160 |
| | | HCl pH 2 | 134 | 134 | 134 | 145 |
| 9 | 100μg/ml. | Phosphate pH 7 | 86 | 98 | 88 | 83 |
| | | HCl pH 2 | 60 | 63 | 66 | 103 |
| 11 | 100μg/ml. | Phosphate pH 7 | 100 | 94 | 94 | 100 |
| | | HCl pH 2 | 51 | 55 | 27 | 12 |
| 13 | | Phosphate pH 7 | 10 | 10 | 10 | 10 |
| | 100μg/ml. | HCl pH 2 | 10 | 10 | 10 | 10 |
| | 50μg/ml. | Human blood | 0.5 | 1.2 | 1.6 | 1.6 |
| 14 | 100μg/ml. | Phosphate pH 7 | 50 | 80 | 82 | 86 |
| | | HCl pH 2 | 95 | 61 | 42 | 13 |
| 19 | 100μg/ml. | Phosphate pH 7 | 116 | 112 | 118 | 118 |
| | | HCl pH 2 | 110 | 112 | 110 | 110 |
| 21 | 100μg/ml. | Phosphate pH 7 | 10 | 10 | 10 | 10 |
| | | HCl pH 2 | 10 | 10 | 10 | 10 |

EXAMPLE 26

Comparative Data

The peak concentrations in Squirrel monkeys (obtained as described in Example 24) for the compound of Example 1 the N ethoxycarbonyl-N-methyl)aminomethyl ester of Penicillin G is compared in Table III with the corresponding peak values for other known esters of Penicillin G

TABLE III

| Compound | Peak concentration in Squirrel monkeys assayed as Penicillin G (μg/ml) |
|---|---|
| Compound of Example 1 | 17.2 |
| Acetoxyα-methyl methyl ester | 5.7 |
| Acetoxymethyl ester | 4.2 |
| pivaloyloxymethyl ester | 3.9 |
| Penicillin G | 3.1 |

We claim:

1. A compound of formula (I) or a pharmaceutically acceptable acid-addition salt thereof which contains a basic nitrogen atom:

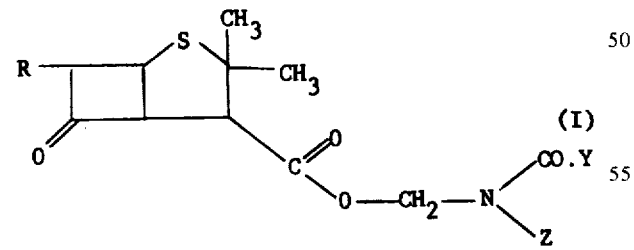

(I)

wherein
Y is alkyl of one to six carbon atoms, phenyl, benzyl, alkoxy of one to six carbon atoms, or benzyloxy;
Z is alkyl of one to six carbon atoms, phenylbenzyl, alkoxy of one to six carbon atoms, cyclopentyl, cyclohexyl and phenyl, or Y+Z taken together are a 3-benzoxazolidine ring;
R is phenylacetamido, 2- or 3-thienylacetamido, phenoxyacetamido, α-amino-phenylacetamido, α-amino-2- or 3-thienylacetamido, α-carboxyphenylacetamido, α-sulphophenyl-acetamido, α-azidophenylacetamido, α-guanidinophenylacetamido, or N-tetrazolylacetamido, provided that: when Z is hydrogen, Y is alkoxy of one to six carbon atoms then R is not a group of formula (IV):

(IV)

in which $R_1$ is $C_{2-7}$ alkyl, phenyl, or furyl.

2. A compound as claimed in claim 1 wherein R is phenylacetamido, 2- or 3-thienylacetamido, α-aminophenylacetamido or N-tetrazolylacetamido.

3. A compound as claimed in claim 1 wherein Y is a $C_{1-6}$ alkoxy or benzyloxy group.

4. A compound as claimed in claim 1 wherein Z is $C_{1-6}$ alkyl, cyclopentyl or cyclohexyl.

5. A compound as claimed in claim 5 wherein Z is methyl.

6. A compound selected from the group consisting of:
N-Benzoylaminomethyl ester of penicillin G
3-Benzoxazolidinone methyl ester of penicillin G
N-Acetylaminomethyl ester of penicillin G
N Propionylaminomethyl ester of penicillin G
Benzoxazolidinone -3-methyl ester of ampicillin hydrochloride.

7. (N-Ethoxycarbonyl-N-methyl)amino-methyl ester of penicillin G.

8. (N-Acetyl-N-methyl)aminomethyl ester of penicillin G.

* * * * *